United States Patent [19]

Torma et al.

[11] Patent Number: 5,365,425
[45] Date of Patent: Nov. 15, 1994

[54] METHOD AND SYSTEM FOR MEASURING MANAGEMENT EFFECTIVENESS

[75] Inventors: Michael J. Torma, Dallas, Tex.; Bernard W. Galing, Papillion, Nebr.; Robert J. Palmer, Omaha, Nebr.; Suzanne K. S. West, Bellevue, Nebr.

[73] Assignee: The United States of America as represented by the Secretary of the Air Force, Washington, D.C.

[21] Appl. No.: 52,402

[22] Filed: Apr. 22, 1993

[51] Int. Cl.[5] .............................. G06F 15/42
[52] U.S. Cl. .................. 364/401; 364/413.13
[58] Field of Search .............. 364/402, 401, 413.01

[56] References Cited

U.S. PATENT DOCUMENTS

| | | | |
|---|---|---|---|
| 4,667,292 | 5/1987 | Mohlenbrock et al. | 364/406 |
| 4,858,121 | 8/1989 | Barber et al. | 364/406 |
| 4,893,270 | 1/1990 | Beck et al. | 364/900 |
| 4,975,840 | 12/1990 | DeTore et al. | 364/401 |
| 4,992,939 | 2/1991 | Tyler | 364/401 |
| 5,063,506 | 11/1991 | Brockwell et al. | 364/402 |
| 5,117,353 | 5/1992 | Stipanovich et al. | 374/401 |
| 5,128,860 | 7/1992 | Chapman | 364/401 |
| 5,212,635 | 5/1993 | Ferriter | 364/402 |
| 5,216,519 | 6/1993 | Nemirousky et al. | 364/402 |
| 5,278,751 | 1/1994 | Adiano et al. | 364/402 |
| 5,280,425 | 1/1994 | Hogge | 364/402 |

Primary Examiner—Gail O. Hayes
Attorney, Agent, or Firm—Donald J. Singer; William G. Auton

[57] ABSTRACT

A system and process are presented in which the factors of quality, cost, and access are integrated in such a manner as to provide a holistic description of the effectiveness of care at medical treatment facilities (MTFs). By using medical treatment data from a variety of computerized databases and incorporating patient perceptions of care through the use of surveys, the effectiveness of a particular facility's medical care can be compared to other medical care facilities. Deficiencies in performance are readily identified through this process, permitting goals and targets to be established that provide direction for medical administrators to enhance medical care at their treatment facilities. This approach is applicable to any set of medical care facilities, and also to just about any organized human endeavor involving quality, cost and access factors.

18 Claims, 4 Drawing Sheets

ADJUSTMENTS TO QUALITY

QIP INDICATOR DISTRIBUTION

ADJUSTMENTS TO QUALITY

SEVERITY INDEX DISTRIBUTION

CASE WEIGHT DISTRIBUTION

SEVERITY INDEX DISTRIBUTION

DIRECT COST : TOTAL COST DISTRIBUTION

"IN THE GREEN PERFORMANCE":
HIGH QUALITY
HIGH ACCESS
LOW COST

METHOD AND SYSTEM FOR MEASURING MANAGEMENT EFFECTIVENESS

STATEMENT OF GOVERNMENT INTEREST

The invention described herein may be manufactured and used by or for the Government for governmental purposes without the payment of any royalty thereon.

BACKGROUND OF THE INVENTION

This invention relates generally to a method and system for utilizing management effectiveness, and more specifically to a method and system for providing medical care at a reasonable cost for all the nation's citizens. Existing tools, which focus on single measurement parameters in isolation, do not convincingly capture the way health care facilities operate. At least in part for this reason, such tools have failed to inspire significant practice pattern changes and/or management efficiencies, even in light of the current furor over U.S. health care spending. Therefore, we designed and developed a method and system of integrated medical organizational performance across the parameters of quality, cost, and access. Without a complete understanding by medical managers of these underlying issues of medical care, solutions to the medical problems of this country are not achievable. Large scale improvements in the current state of medical care require a standard which compels management's attention to the proper balance between these competing but interrelated forces.

The task of evaluating the factors of quality, cost, and access in such a manner as to provide a holistic description of the effectiveness of medical treatment data, is alleviated, to some extent, by the systems disclosed in the following U.S. Patents, the disclosures of which are incorporated herein by reference:

U.S. Pat. No. 5,128,860 issued to Chapman
U.S. Pat. No. 5,117,353 issued to Stipanovich et al.
U.S. Pat. No. 4,992,939 issued to Tyler
U.S. Pat. No. 4,975,840 issued to Detore et al.
U.S. Pat. No. 4,893,270 issued to Beck et al.
U.S. Pat. No. 4,858,121 issued to Barber et al.; and
U.S. Pat. No. 4,667,292 issued to Mohlenbrock et al.

The patent to Mohlenbrock et al. discloses patient billing for hospital care. The computer billing is reviewed by the physician each day. The patent to Beck et al. discloses a medical information updating system for patents. The patent to Tyler discloses a method of producing a narrative report. The Tyler system analyzes information which has been inputted to a database and using predetermined phrases intermingled with extracts from the database, produce a narrative analytical report which describes the critical aspects of the database. The Tyler system also produces a listing of questions on those aspects of the database which require explanation of clarification. The patents to Barber et al., Detore et al., Stipanovich et al., and Chapman are of interest, but they do not model medical care facilities (MTFs) based on quality of care, cost, and access.

Currently, medical care is not evaluated in a holistic manner. Instead, quality is examined in isolation from cost and neither of these is compared to access which is rarely, if ever, evaluated. In addition, there is a lack of commonality between the evaluation criteria that do exist, making comparisons between treatment facilities and medical practitioners infeasible. As a result, goals for improvements in medical care cannot be established except in individual hospitals.

In terms of cost, there are many criteria that are used, whether for the cost of supplies or provider charge rates. Since none of these cost criteria are universal, it is difficult to compare different hospitals on the basis of cost. Also, accounting practices differ causing further complications. To make medical care affordable for all people in this country, it is imperative that definitions of cost be standardized.

Quality of medical care is almost universally defined in terms of mortality rates, which has not proven to be very useful. At least one study has indicated that even the best hospitals can now and then have unfavorable mortality rates. When using mortality figures to evaluate quality of care, it is important to separate those that were expected to die from those that were not. This is not currently done and is not easy to do, especially in terms of the litigation such a practice would cause in insurance and medical industries (i.e. lawsuits over those persons that should not have died). As a result, mortality in and of itself does not describe "quality" medical care and is not a useful metric to use to try to solve the medical problems facing this country.

Access to medical care is not directly measurable. Since there are many hospitals and medical practitioners from which to choose, at least in urban areas, it would be infeasible to attempt to associate the number of people that should have access to a particular hospital or doctor. The only "measurable" criteria for access to medical care are media accounts and government estimates of people who have little or no medical insurance and thereby are assumed to have a lack of access to medical care. Again, definitions are important since medical care is available, its just that people cannot afford it.

To assess how well a hospital or doctor provides medical care, and to establish the cost effectiveness of that care, the three factors of quality, cost, and access must be evaluated simultaneously. Current methods of measuring these factors are lacking and provide little useful information to the medical manager. Without an overall perspective of how these factors interrelate and how an improvement in one can lead to a change in another, medical managers cannot be expected to achieve improvements that would lead to a cost effective medical care program for everyone in the country.

SUMMARY OF THE INVENTION

The invention is a process and system of modeling the factors of quality, cost, and access in such a manner as to provide a holistic description of the effectiveness of medical treatment data from a variety of computerized databases and incorporating patient perceptions of medical care through the use of surveys. This allows effectiveness of different groups of medical care facilities to be compared to each other. Deficiencies in performance are readily identified through this process, permitting goals and targets to be established that provide direction for medical administrators to enhance medical care at their treatment facilities.

One embodiment of the invention may be considered a process for evaluating effectiveness of service among a set of treatment facilities, the process includes the steps of: gathering data quantifying quality, cost, and access performances characteristics of each of the treatment facilities; displaying the quality, cost and access performance characteristic simultaneously on a graph to indicate thereby strong and weak quality, cost and access performance characteristics; and identifying the strong and weak quality, cost and access performance characteristics of each treatment facility.

To ensure that all medical treatment facilities are considered fairly, adjustments are made to the data based on patient severity of illness, the amount of resources used for treatment (case weight), and the ratio of direct military care costs to CHAMPUS costs. These adjustments are applied to equations that have been developed for each of the three factors (quality, cost, and access), providing a quantitative three dimensional cube permitting managers to assess the overall effectiveness of their treatment facilities. For simplicity, each factor is divided into "High" and "Low" regions.

Another embodiment of the invention is a system for evaluating effectiveness of service among a set of treatment facilities. This system uses commercially-available computers as a means for gathering data quantifying quality, cost, and access performances characteristics of each of the treatment facilities. This system uses a central computer as a means for identifying the strong and weak quality, cost and access performance characteristics of each treatment facility. The central computer is also an ordinary computer with a computer monitor that serves as a means for displaying the quality, cost and access performance characteristics simultaneously on a graph to indicate thereby strong and weak quality, cost and access performance characteristics. The central computer is programmed to depict the quality, cost and access performance characteristics in a chart that simulates a three-dimensional cube which has a separate axis for the quality, cost, and access performance characteristics.

The object of the invention is to provide a system and process that evaluates the quality cost and access of treatment facilities, and identify deficiencies thereby.

This object together with other objects, features and advantages of the invention will become more readily apparent from the following detailed description when taken in conjunction with the accompanying drawings wherein like elements are given like reference numerals throughout.

DETAILED DESCRIPTION OF THE PREFERRED EMBODIMENT

The present invention can be regarded as a process and system for identifying possible deficiencies among a set of treatment facilities. The process includes the steps of: measuring actual quality, cost and access performance characteristics of the treatment facilities; establishing standards of performance values for quality, cost and access for the treatment facilities; and comparing the actual quality, cost and access performance characteristics of each of the treatment facilities with the standards of performance values of quality, cost and access to identify thereby the possible deficiencies in the treatment facilities.

In this process, each of the treatment facilities is a medical treatment facility, and the measuring step for quality is performed using a Quality Indicator Project service which provides the measure of quality performance characteristics for each medical treatment facility. Also in this process, the measure of quality and cost performance characteristics are adjusted for both patient perception of treatment and for severity of illness to produce thereby the actual quality performance characteristics of each medical treatment facility. Finally note that the establishing step is performed by producing the standards of performance values by averaging the quality, cost and access performance characteristics to produce a set of average values, and wherein the company step is performed by counting magnitudes of deviation between the actual quality, cost and access performance characteristics and their respective averages among the set of average values.

As discussed below, the present invention can also be considered a system which performs the steps recited above using a distributed computer network.

Figure 1:
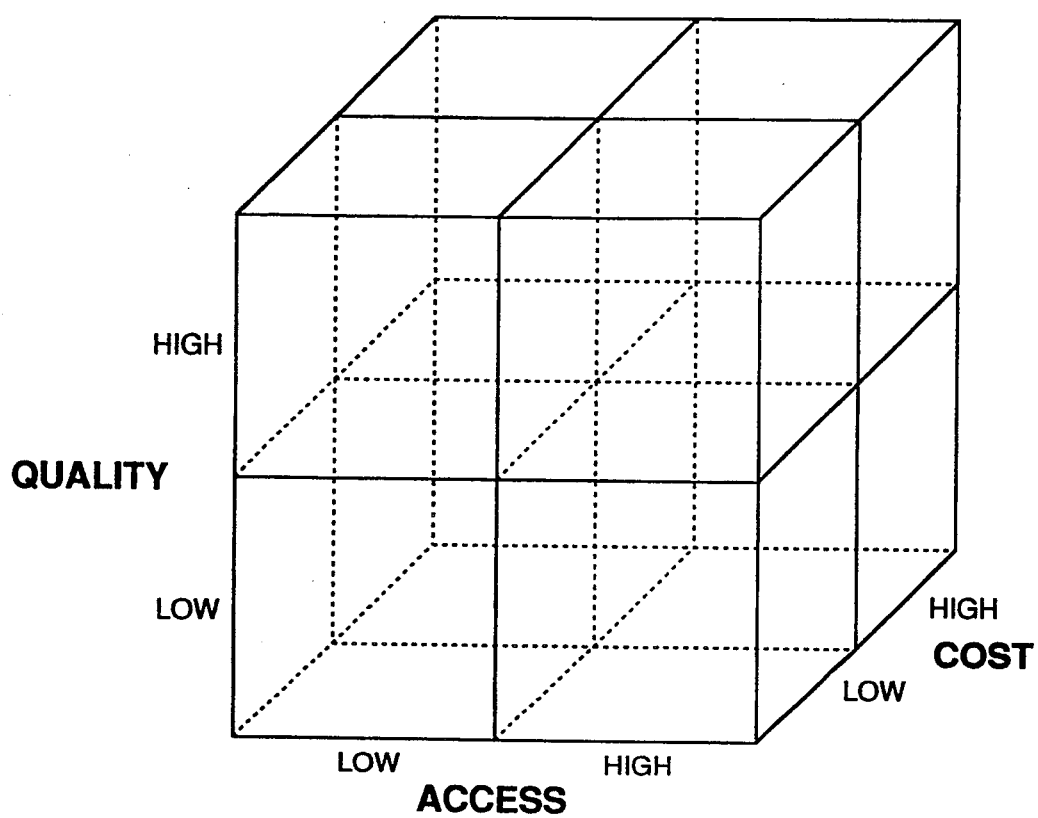
FIG. 1 is an illustration of a cube used in the invention to depict quality, cost and access graphically.

The interrelated factors of quality, cost, and access suggested a three dimensional relationship, for example a response surface, since each measure is conceivably continuous. For simplicity, however, criteria were established so as to access each factor as being favorable or unfavorable. As such, a cube of eight octants is used to simultaneously depict graphically the factors of quality, cost, and access as shown by FIG. 1. For example, a treatment facility that was the most effective would meet or exceed established criteria for each of these measures (i.e. high quality, low cost, high access). Treatment facilities that are deficient in meeting the established performance goal in one or more measures would indicate that some level of improvement is warranted. Visually, by color coding the octants of the cube (all favorable="green", one unfavorable="yellow", two or more unfavorable="red"), the overall performance of the treatment facility would be readily apparent, making the representation a useful management tool.

It is important to note, however, that placement in the cube does not necessarily indicate good effectiveness. For example, a treatment facility that did not meet the criterion established for "quality" does not mean that the facility exhibited poor quality, per se. This is only an indication that performance appears to be below established values. The reasons for this less than desired performance could then be explored, and possibly explained satisfactorily by circumstances not encompassed by the model.

As lower rated treatment facilities improve in quality, the criterion would be adjusted upward so that it continues to allow discrimination between higher and lower levels of performance. The treatment facilities, therefore, should not only attempt to meet established criteria, but should seek continued improvement since the criteria will eventually reflect higher overall expected levels of performance.

Conceptually, the positioning of a treatment facility in the cube is indicative only of relative rating. However, by using data gathered from several sources, a more complete picture of facility performance can be shown. Of the three measures of performance, cost and access can be measured objectively. A quality measure, however, is much more subjective. Nevertheless, objective data are available that can be useful in this regard.

Quality is both an actual fact and a perception on the part of the patient. If a patient actually receives quality care but perceives it otherwise, the patient is apt not to elect future treatment from the facility or the provider, adversely affecting the access measure. Nevertheless, the emphasis should remain with actual quality of care as evidenced by data from the treatment facility, perhaps with some adjustment for patient perceptions. The method used here for examining quality of care is the Maryland Quality Indicator Project (QIP), to which a number of civilian and Department of Defense (DOD) hospitals are subscribers. Using data from hospitals nationwide, ten indicators have been selected as measures of quality. However, these indicators do not account for severity of illness or resource usage (case mix), which must be considered when performing comparisons between treatment facilities.

Equation 1, as presented below, denotes the process by which quality is calculated. Note that it is a summation over all ten QIP quality measures, adjusted first for severity of illness and then measured in terms of magnitude of deviation from an average value. This permits different treatment facilities to be compared on an equal basis.

$$\text{Quality} = \sum_{i=1}^{10} \left( \frac{\beta_i I_i - \mu_i}{\sigma_i} \right) + \epsilon \quad (1)$$

where i is the QIP indicator $\beta$ is an adjustment factor based on an average severity indexing for a particular treatment facility I is the QIP indicator value at a particular treatment facility $\mu$ is the mean value of the QIP indicator for all treatment facilities $\sigma$ is the standard deviation of a QIP indicator based on all treatment facilities $\epsilon$ is a patient perception adjustment factor (−0.1,0,0.1)

As mentioned above, the method used here for examining quality of care uses the Maryland Quality Indicator Project (QIP), to which a number of civilian and Department of Defense (DOD) hospitals are subscribers. Using data from hospitals nationwide, ten indicators have been selected as measures of quality. These indicators are shown in Table 1 but they do not account for severity of illness or resource usage (case mix), which must be considered when performing comparisons between treatment facilities.

TABLE 1

QUALITY INDICATORS

| I | Hospital Acquired Infections |
|---|---|
| II | Surgical Wound Infections |
| III | Inpatient Mortality |
| IV | Neonatal Mortality (1801 grams only) |
| V | Perioperative Mortality |
| VI | Cesarean Sections |
| VII | Unplanned Admissions Following Ambulatory Procedure |
| IX | Unplanned Returns to Special Care Unit |
| X | Unplanned Returns to Operating Room. |

Equation 1 denotes the process by which quality is calculated. Note that it is a summation over all ten QIP quality measures, adjusted first for severity of illness and then measured in terms of magnitude of deviation from an average value. This permits different treatment facilities to be compared on an equal basis.

As indicated by Equation 1, if a quality indicator for a particular treatment facility is lower than the average of that quality indicator across all treatment facilities, then the result is a negative number; otherwise, it is positive. This would indicate that an overall negative value for the quality measure suggests a facility that exhibits better than average quality. A positive value would indicate quality that is less than average. Therefore, it would seem appropriate to place treatment facilities in the cube based on negative (green) or positive (red) values of the quality measure. It was decided to treat all ten QIP quality measures equally (i.e. no one quality measure is more important than another).

Severity indexing is used to account for differences in patients and treatments. As severity increases, the differences between a particular treatment facility's quality indicator and the average quality indicator becomes more marked. That is, if two facilities have negative indications of quality, but the second facility treats patients with more severe illnesses than does the first, then the second facility would be given credit for higher quality of care.

Figure 2A:
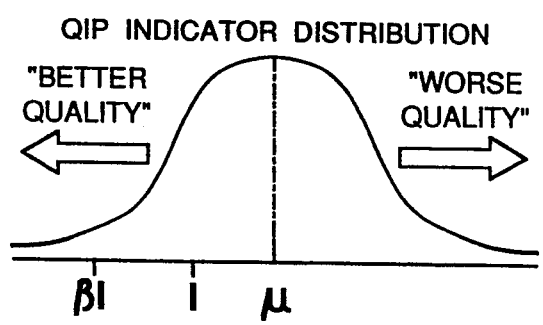
FIGS. 2A and B are charts depicting how the QIP indicator is adjusted for patient perception (FIG. 2A) and for the severity index effect (FIG. 2B)

Shown in FIGS. 2A and B is the process whereby the adjustment factor for quality ($\beta$ in Equation 1) is calculated. Each treatment facility receives a score, denoted by "I" in FIG. 2A for each of the ten quality indicators used by the Maryland Quality Indicator Project. The value "$\mu$" represents the average score for all hospitals for a particular quality indicator. Thus, if a hospital has a lower value than the average for all hospitals, then this particular hospital would have "better" quality for this particular quality indicator.

However, other circumstances could affect this comparison. If the hospital in question treats patients that are not as sick as those that are treated at other hospitals, it would be expected that the quality of this hospital would be better since the patients are not as sick. In this instance the full benefit of being better than average should not be given, but should be reduced. On the other hand, if the patients seen at this hospital are sicker than those seen at other hospitals, and this hospital is also better than average, then extra credit should be given.

Figure 2B:
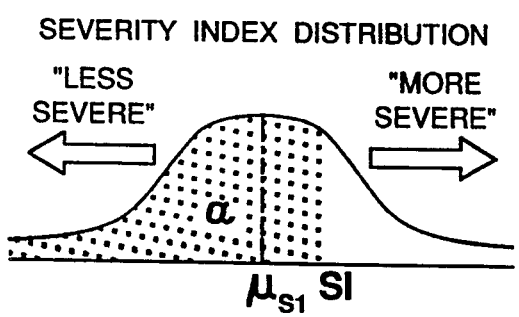

Adjustments for severity of illness are represented by the value $\beta$. Each of the ten quality indicators can be associated with a Diagnostic Related Group (DRG), Medical Diagnostic Code (MDC), or other medical grouping which can be used to assess each patient in the group and thereby calculate a severity index (SI) for each quality indicator. Then, an average SI (represented by $\mu_{SI}$) can be calculated for each quality indicator, permitting a comparison of severity levels between a single hospital and an average severity levels for all hospitals. As indicated in FIG. 2B, if the severity index of patients at a hospital (represented by "SI") is greater than the average for all hospitals, then extra credit will be given to that hospital for treating a more severe case of patients.

It is assumed that severity levels will follow a Gaussian, or normal, distribution. By simply using the area under the normal distribution an adjustment factor for quality can be calculated. When the severity index (SI) for a hospital for a quality indicator is compared to the average for all hospitals, a certain amount of area is covered under the normal distribution. The amount of area will vary between 0 and 1 and is designed by $\alpha$. We have arbitrarily set $\beta$, the quality adjustment factor, equal to 1.5 minus $\alpha$ ($\beta = 1.5 - \alpha$). Thus, if the severity index of a hospital was exactly that of the average for all hospitals, then $\alpha = 0.5$ which results in $\beta = 1$ (i.e. no adjustment will be made). Similarly, if the severity index for a hospital is greater than average, then $\alpha$ is greater than 0.5 which would cause $\beta$ to be less than one ($\beta < 1$). This would shift the quality measure of the hospital ("I") to the left. Referring to FIG. 2, in the case of a hospital with "better quality" such an adjustment would mean an even better quality value than indicated by "I" alone. In a similar fashion, if the severity index of a hospital was less than average (i.e. the hospital treats less sick patients), then $\alpha < 1$ which causes $\beta > 1$, causing a shift to the right of the hospital quality indicator value. This indicates that quality at this hospital for this particular quality indicator is not as good as it seems.

Since there are ten quality indicators, there will be ten $\alpha$ values and ten $\beta$ values for each hospital. For each quality indicator there will also be a standard deviation. By converting all quality indicator values to a standard normal value, and by treating all ten indicators equally in terms of importance, all ten standardized values can be added together. If the result is a negative value, this indicates that, overall, the hospital is performing better than average and should be given a "high" quality rating. If the result is a positive value this indicates worse performance than average and the hospital would be given a "low" quality rating.

This procedure is applicable to other than the normal distribution. Initial indications are that severity and quality indicators follow a normal distribution, at least in terms of assessing hospitals and not individual patients or medical practitioners. The process of calculating quality would not change under conditions of other than a normal distribution. In this instance, another distribution would need to be substituted for the normal distribution and a standardized value for each quality indicator would need to be calculated. The $\alpha$ value would then correspond to the distribution that was being used.

A final adjustment is made to the overall quality measurement by including the patient's perception of quality based on after-treatment patient surveys. While the proper magnitude of this adjustment has not been statistically validated, it is necessary, in principle at least, to allow some form of patient input in quality assessment. While the patient may not fully comprehend the meaning of "quality" care, and whether or not he or she is receiving it, these perceptions carry some weight when determining what provider to use for subsequent treatments. Furthermore, if a patient is not satisfied with the quality of his or her care, the chances for a full and complete recovery could be impaired. Since initial calculations have shown quality values to range from about $-2$ to $+2$, the following patient perception additive values have been assigned (these account for about 5% of the quality measure):

+0.1 if the patient surveys rate poor or very poor
0 if the patient surveys indicate a neutral response
−0.1 if the patient surveys rate good or very good Cost is a relatively easy component to determine for civilian hospitals, at least in terms of how much was spent for x-rays, supplies, physician charges, and so forth. For military medical facilities, on the other hand, cost is perhaps the most difficult to define and measure. While it is known how much is spent overall in a military treatment facility, financial records do not reflect itemized costs as is done in civilian hospitals. As a result, only approximate values can be placed on the cost for providing care for individual patients in military facilities.

To compare one facility to another in terms of cost, it is necessary to first delineate the cost per patient, adjusted for case complexity and severity of illness, for both inpatient and outpatient care. These figures would then provide a foundation for comparing hospitals. In addition, the cost of CHAMPUS inpatient and outpatient care must also be examined (CHAMPUS is a military insurance program for care at civilian facilities). If two facilities have the same internal costs for direct care but the first has a higher per patient cost for CHAMPUS care, then this shortcoming needs to be addressed.

In a manner similar to that used by civilian hospitals, and described in "The Olmstead County Benchmark Project: Primary Study Findings and Potential Implications for Corporate America," *MAYO Clinic Proceedings*, January 1992, the disclosure of which is incorporated herein by reference the cost per eligible beneficiary is used to compare hospital costs. As such, these costs need to be differentiated by direct military care and CHAMPUS care and by inpatient and outpatient care. Equation 2 describes how these costs are computed.

$$\text{Cost} = \sum_{i=1}^{2} (\beta_i I_i - \mu_i) \quad (2)$$

where
  i is the inpatient/outpatient indicator
  $\beta$ is an adjustment factor for case weight, severity, and the ratio of direct military cost to total military cost
  I direct military cost per catchment area employee
  $\mu$ is the benchmark cost against which facility costs are compared By assessing both direct military care and CHAMPUS costs across both inpatients and outpatients, the total cost per beneficiary in a military medical service area can be computed. Obviously, the lower the cost, the better. However, direct costs vary between treatment facilities as do CHAMPUS charges, based partly on the demographics of the beneficiary population. In addition, insurance costs can differ based on regional concerns. To more properly balance the costs associated with each military treatment facility and the military beneficiaries it serves, severity and case complexity are used to adjust the cost of medical care.

In a manner similar to the adjustment for quality, an adjustment is also made to cost. Unlike the quality adjustment, however, several factors need to be considered for cost of medical care. First, severity of illness is important for the same reasons it was important to quality considerations. The severity index is applied to cost in the same manner as it was applied to the quality measure.

In addition, the cost of resources is important. This is termed "case weight" and is different from severity indexing. For example, a person could be severely ill (i.e. a terminally ill cancer patient) but require few resources. On the other hand, an individual with a broken leg could consume many resources (x-rays, plaster casts, etc.) but would not be severely ill. An average case weight for all hospitals can be computed as was done with severity indexing. Again, a normal distribution is assumed for case weight (initial tests show this assumption to be valid) and a standard deviation is computed. An $\alpha$ value is computed based on the area under a normal distribution using the case weight for each hospital being evaluated.

A third adjustment factor concerns the cost of direct versus indirect medical care for military beneficiaries. Total costs for direct care (care given in military facilities by military physicians) are computed as well as the costs of indirect care (through CHAMPUS) by civilian physicians. The ratio of direct costs to total costs (direct plus indirect) provides an indication of the cost to the military of taking care of its beneficiaries. As this ratio approaches the value "1" the more effectively the military is taking care of its beneficiaries in its own facilities. Again, indications are that this ratio follows a normal distribution for which calculations can be made in a fashion similar to that of the quality adjustment.

Figure 3A:
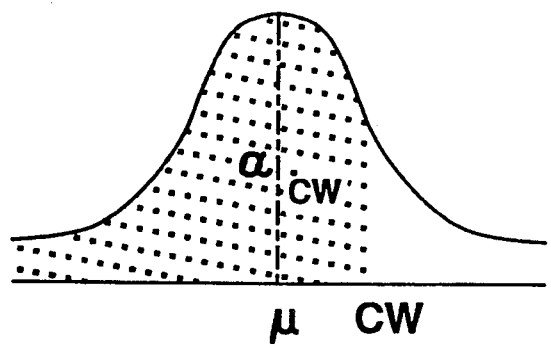
FIGS. 3A, 3B and 3C are charts of adjustments to cost.
Figure 3B:
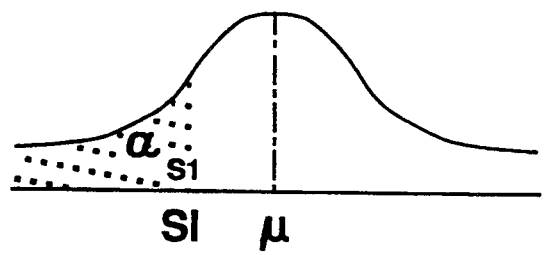
Figure 3C:
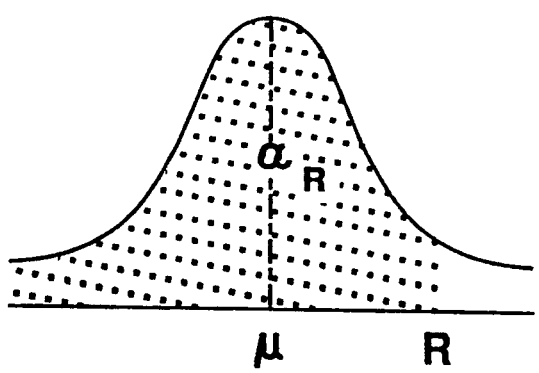

Shown in FIGS. 3-C is the process for calculating the adjustment factor for cost. The $\alpha$ values indicate the distributions being assessed. For example, $\alpha_{SI}$ indicates the area under the normal distribution for severity indexing, $\alpha_{CW}$ is the area under the normal distribution for case weight, and $\alpha_R$ is the area under the normal distribution for the ratio of direct military medical care costs to the total costs of military medical care. As with the quality adjustment, each of these $\alpha$ values is subtracted from 1.5 which permits up to a 50% adjustment for each value. The resultant adjustment factor, $\beta$, is a product of these values. Thus, it is possible to adjust costs by ±337.5% of the actual value for cost. In practice, the adjustment is much smaller. However, if a hospital had very severely ill patients, used many resources, and had a ratio approaching "1" of direct costs to total costs yet still operated below the average cost for all hospitals, then a very large favorable adjustment surely would be appropriate for this facility.

Although accounting practices in the military differ widely from those used in the civilian sector, it is possible to compare military-medical costs on a per patient basis with similar costs in civilian hospitals. In addition, by using the procedures described here, it is possible to compare military treatment facilities with one another. By choosing an established normative cost figure, such as that in the Olmstead study, military treatment facilities can be assessed as having low (green) or high (red) costs for the purpose of placing them in the medical care cube.

Access measures the degree to which military beneficiaries are able to seek and receive treatment at a military treatment facility for both inpatient and outpatient care. In this sense it is also a measure of the capacity of the military treatment facility in terms of inpatient beds and outpatient appointments available. Family members unable to receive care at a military treatment facility seek medical treatment through CHAMPUS. Thus, there is a "lost opportunity" cost associated with not having the capability or resources to treat patients at a military treatment facility.

The development of a quantitative measure for access incorporates the idea of lost opportunity. For inpatients, the lost opportunity consists of those inpatients opting for CHAMPUS when room is available for treatment at the military treatment facility. However, it is not anticipated or desired that a military treatment facility operate at 100% of bed capacity. Because of variations in ward sizes and functions, a more appropriate goal is a 85% bed utilization rate. Therefore, the difference, per day, between how many beds are filled when compared to the desired 85% bed utilization rate and the number of patients using CHAMPUS, forms the basis for the access measure.

The measure of access for outpatients is developed similarly. In this instance, the lost opportunity is derived from the number of outpatients unable to receive an appointment at a military treatment facility. Again, it is not anticipated that 100% of available appointments should be filled. However, it is not unreasonable to expect that 98% should and could be filled. The difference between actual military treatment facility appointments and the 98% goal represents lost opportunity if patients have used CHAMPUS.

However, depending on circumstances, it is conceivable that a military treatment facility could see more outpatients than it actually has available appointments. This could be due, for example, to doctors and staff working overtime or to an unexpected influx of patients requiring immediate care. In such cases the access measure could be greater than the planned appointment utilization rate (for example, a military treatment facility could show 105% access).

Equation 3 formalizes the relationship for access as a function of lost opportunity and patient perception.

$$\text{Access} = \sum_{i=1}^{2} \left( \frac{C_i + D_i - G_i R_i}{C_i} \right) + \epsilon \qquad (3)$$

where i indicates inpatient or outpatient

C is CHAMPUS average daily patient load or outpatient visits

D is military hospital average daily patient load or outpatient visits

G is the goal for bed utilization or outpatient appointments

R is the number of beds in the military hospital or the number of available appointments $\epsilon$ is an adjustment for patient perception of access to military direct care ($-0.1, 0, 0.1$)

In this equation, the numerator represents the number of inpatients or outpatients that could not have been seen at the military treatment facility since space would not have been available, either in terms of beds or appointments. Lost opportunity then equates to the ratio of those patients for which direct military treatment facility care was unavailable to the total number of patients that were seen through CHAMPUS (indicated by C in Equation 3).

If military treatment facilities exactly meet their goals for inpatient bed utilization and outpatient appointments, then the value for access would be 2 (i.e. the ratio would be one for both inpatient and outpatient measures). In theory, then, a military treatment facility's placement in the cube depends upon whether or not it was above or below the value "2". If it had a value greater than 2, then access would be good (green), otherwise it would be poor (red). In addition, since patient perceptions are valid in addressing access issues, an adjustment to the access values can be made depending on patient survey responses. As with the quality perception, such a value is as yet statistically unproven. However, by assigning a value of ±0.1 for exceptionally good or poor survey results, patient perception would comprise about 10% of the overall access value, which is not unreasonable.

Several conclusions concerning inpatient care can be drawn from the results of the access equation. If the value for access is close to unity, then the military treatment facility is reaching its goal of 85% bed utilization yet patients continue to seek care through CHAMPUS. This could indicate that additional beds need to be added to the military treatment facility through construction and/or increased staffing. Access in this instance would be good (green) since the military treatment facility would be operating at desired capacity.

If, on the other hand, the access value is low, then some problem exists which motivates patients to seek inpatient care outside the military treatment facility. This could correlate with quality issues as discussed previously, requisite specialties at the military treatment facility could be lacking, or the granting of CHAMPUS care is excessive and would need to be curtailed.

Outpatient conclusions can also be drawn. If appointments are not filled then perhaps staffing is too high. If appointments are missed, then there may be scheduling or leadership issues that must be addressed. If appointments met exceeds 100% then staffing and scheduling problems may exist.

Figure 4:
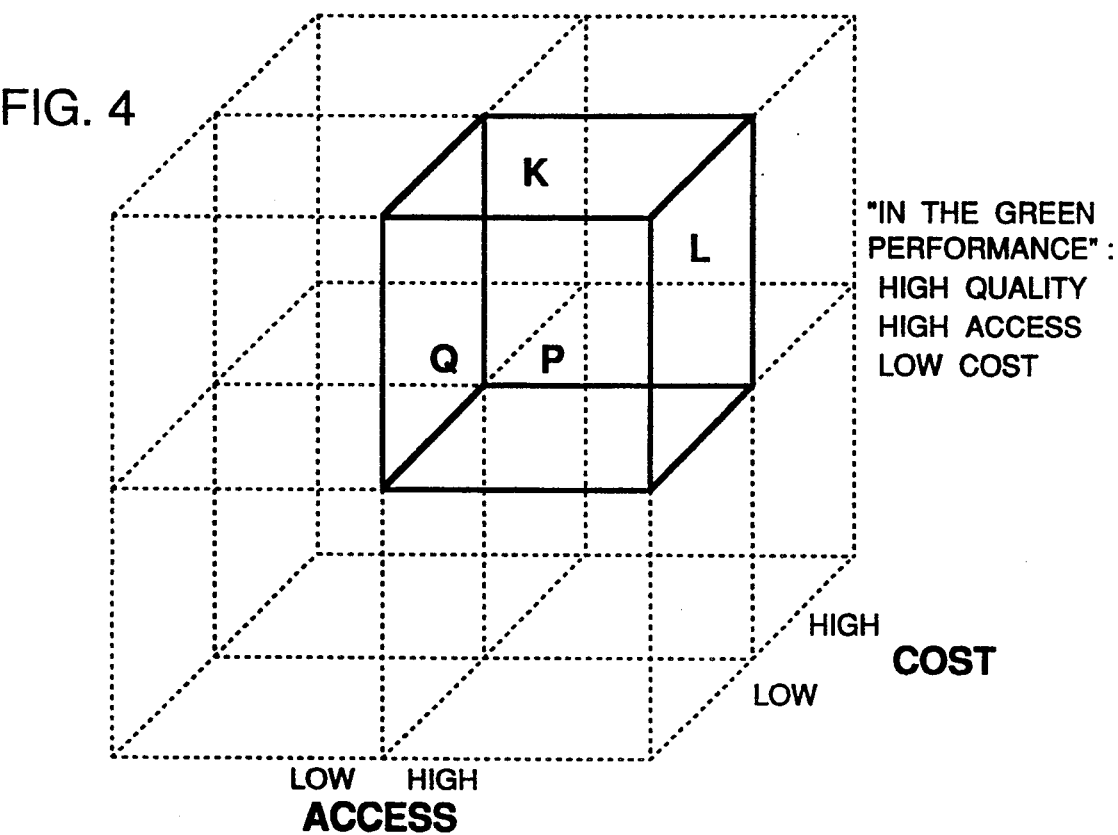
FIGS. 4 and 5 respectively illustrates the use of the cube of FIG. 1 to chart top and bottom performing treatment facilities.

Initially, this model was used to evaluate military medical treatment facilities for the Strategic Air Command (SAC). Cost, quality, and access data was collected from Department of Defense (DOD) data bases for the 22 military treatment facilities assigned to SAC and then used with the equations described above. Results indicated that there was a wide spectrum of hospital performance, although all SAC treatment facilities exhibited low cost when compared to established civilian norms. FIG. 4 indicates the three SAC treatment facilities that had the best performance—high quality, low cost, and high access—which we have termed "in the green performance".

Figure 5:
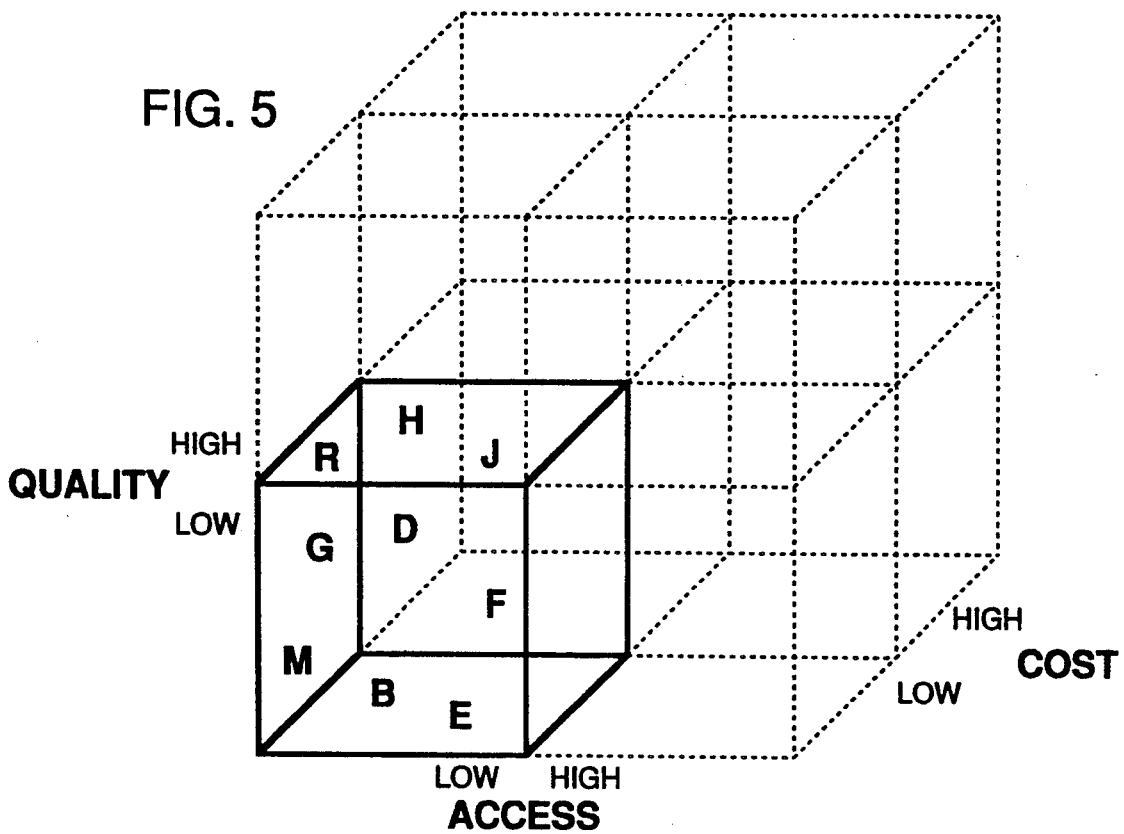

The treatment facilities shown in FIG. 4 have been coded with designated letters. These facilities can now be examined to determine appropriate staffing levels, practices and procedures, and other aspects that set these facilities apart from the others. Likewise, the other 19 SAC hospitals that did not meet the established standards can be examined to determine where improvements are necessary. FIG. 5 illustrates several SAC hospitals that were deficient in both quality and access.

Examining facility M in further detail, it was possible to establish several goals, the attainment of which would cause this facility to move into the best performing group. To improve quality, this facility would need to reduce hospital acquired infections (QIP I), unplanned hospital readmissions (QIP VII), and unplanned admissions following ambulatory procedures (QIP VIII) by at least 6% over current rates. In terms of improving access, this facility would need to recapture about two CHAMPUS outpatients per day and about one CHAMPUS inpatient per day. These become clear goals for which this facility must strive. It is the job of the hospital commander (administrator) to provide the resources and guidance to attain these goals. Assuming the other rated factors remain constant, such improvements would move this facility into the top performing hospital group.

There are many advantages of using this integrated assessment of medical care. By using this model, a decision maker can, for the first time, evaluate the overall effectiveness of a hospital as well as provider efficiency. In general, these advantages can be grouped into four categories.

At the system level, a high ranking manager (i.e. a CEO) can compare all treatment facilities under his control and identify those that provide overall good medical care from those that may be deficient in one or more areas. By identifying these deficiencies, the manager can allocate resources (money, physicians, etc.) to enhance the effectiveness of those treatment facilities that do not meet established goals.

At the hospital or treatment facility level, an administrator can identify those services that are performing below expectations and allocate resources to assist improvements in these areas. Not only will the administrator know how his or her hospital compares to others in the overall system and where general improvements are required, but he or she will also know which clinics, wards, and other services need improvements.

At the service level (clinics, wards, etc.), the specific procedures that cause deficiencies are noted. Thus, if a clinic performs more Cesarean sections than is considered appropriate, remedial training or other actions can be implemented to improve this situation. These become goals for CQI and many such small improvements can create a large scale shift in overall hospital performance. Furthermore, those clinics that perform better than average can be examined in terms of staffing, procedures, and other activities that set them apart from the rest. These activities can then be applied to similar clinics in other hospitals which in turn can enhance the performance of the other hospitals.

Finally, at the provider level this model becomes a powerful tool for effecting change in practice patterns. As an extension of the example above, if a clinic is performing below average because of Cesarean sections, but only one or two physicians are the cause, then actions can be implemented to help change the practice patterns of these physicians if such changes are warranted.

The interrelationships between quality, cost, and access are depicted graphically and where overall improvements are needed. By examining the top performing treatment facilities, a new and more complete understanding of staffing requirements for physicians, nurses, and other support staff will be possible. An evaluation of access rates and bed utilization will indicate if the current hospital size is appropriate and whether or not expansion is required. By pinpointing those hospitals and physicians that provide the highest quality of care at reduced cost, that factors that make this care possible can be determined and exported to other treatment facilities. As other emulate these top performers, costs of medical care should decline, providing the opportunity for increased access to the health care system.

There currently exist no known alternatives that holistically evaluate medical care across the factors of quality, cost, and access. All hospitals measure cost, although there is no universal method for this measure. Quality is measured based on mortality rates and although the Maryland Quality Indicator Project measures other aspects of quality, this procedure is still used as a stand alone indicator. Furthermore, this Maryland QIP evaluation is for inpatients only and does not address outpatient quality. The use of patient surveys is widespread but, again, these results seem to be used in isolation. Access is almost never measured by prior art systems.

Figure 6:
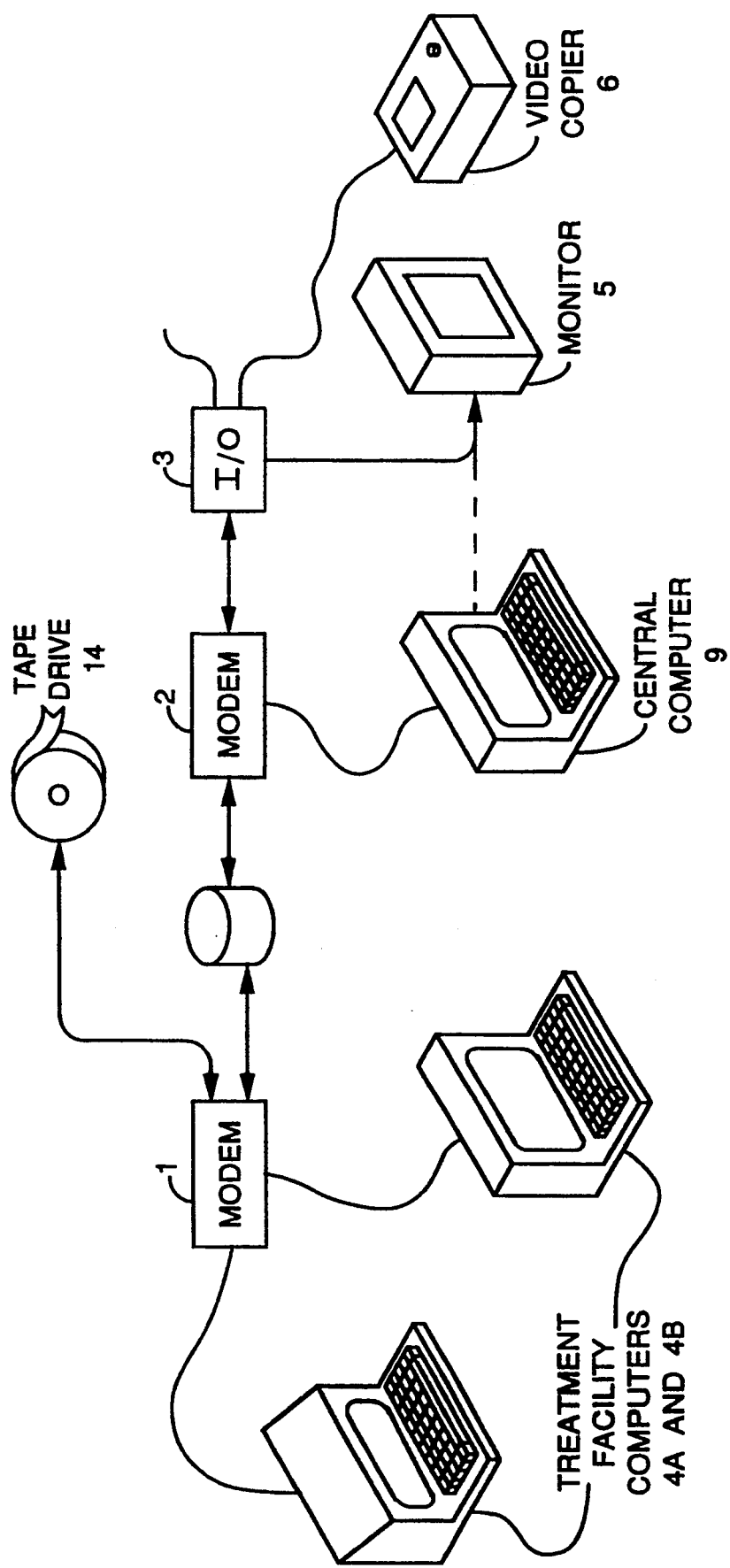
FIG. 6 is a distributed computer data system.

FIG. 6 is a distributed computer data system composed of commercially-available equipment which can be used by the present invention. In FIG. 6, the database for two remote treatment facilities is maintained in their respective computers 4A and 4B. This data is conducted over phone lines by modems 1 and 2 to the central computer 9.

The central computer 9 is programmed to perform Equations 1-3 on the quality, cost and access data it receives to display the cube of FIGS. 1, 4 and 5 on either a monitor 5 or a video copier 6. In the system of FIG. 6, computers 4A and 4B serve as a means for measuring the actual quality, cost and performance characteristics of their respective treatment facilities. Computers 4A and 4B, in the preferred embodiment, made use of the Maryland Quality Indicator Project as described above, and make use of a modem 1 to provide their data to the central computer 9. The central computer 9 is used to establish standards of performance values for comparison with the actual performance characteristics of each of the treatment facilities, and identify possible deficiencies thereby.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A process for evaluating effectiveness of service among a set of treatment facilities, said process comprising the steps of:
    gathering data quantifying quality, cost, and access performance characteristics of each of the treatment facilities;
    displaying the quality, cost and access performance characteristics simultaneously on a graph to indicate thereby strong and weak quality, cost and access performance characteristics; and
    identifying the strong and weak quality, cost and access performance characteristics of each treatment facility.

2. A process, as defined in claim 1, wherein said displaying step is performed using a three-dimensional cube using a separate axis for the quality, cost and access performance characteristics.

3. A process, as defined in claim 2, wherein said displaying step is performed on said graph by charting the quality performance characteristics such that:

$$\text{Quality} = \sum_{i=1}^{10} \left( \frac{\beta_i I_i - \mu_i}{\sigma_i} \right) + \epsilon$$

where:
   i is a quality indicator;
   $\beta$ is an adjustment factor based on an average severity indexing for a particular treatment facility;
   I is a quality indicator value at a particular treatment facility;
   $\mu$ is a mean value of the QIP indicator for all treatment facilities;
   $\sigma$ is a standard deviation for a QIP indicator based on all treatment facilities; and
   $\epsilon$ is a patient perception adjustment factor (−0.1,0,0.1).

4. A process, as defined in claim 3, wherein said displaying step is performed on said graph by charting the access performance characteristics such that:

$$\text{Access} = \sum_{i=1}^{2} \left( \frac{C_i + D_i - G_i R_i}{C_i} \right) + \epsilon$$

where
   i indicates inhouse client;
   C is a preselected average daily client load;
   D is particular hospital average daily client;
   G is the goal for appointments;
   R is the number of available appointments; and
   $\epsilon$ is an adjustment for client perception of access (−0.1,0,0.1).

5. A process, as defined in claim 4 wherein said displaying step is performed on said graph by charting the cost performance characteristics such that are given by:

$$\text{Cost} = \sum_{i=1}^{2} (\beta_i I_i - \mu_i)$$

where:
   i is an inhouse client indicator;
   $\beta$ is an adjustment factor for case weight, severity, and a ratio of direct cost to total cost;
   I direct cost per catchment area employee; and
   $\mu$ is a benchmark cost against which facility costs are compared.

6. A process, as defined in claim 3 wherein said displaying step is performed on said graph by charting the cost performance characteristics such that are given by:

$$\text{Cost} = \sum_{i=1}^{2} (\beta_i I_i - \mu_i)$$

where:
   i is an inhouse client indicator;
   $\beta$ is an adjustment factor for case weight, severity, and a ratio of direct cost to total cost;
   I direct cost per catchment area employee; and
   $\mu$ is a benchmark cost against which facility costs are compared.

7. A process, as defined in claim 2, wherein said displaying step is performed on said graph by charting the access performance characteristics such that:

$$\text{Access} = \sum_{i=1}^{2} \left( \frac{C_i + D_i - G_i R_i}{C_i} \right) + \epsilon$$

where
   i indicates inhouse client;
   C is a preselected daily client load;
   D is a particular hospital average daily client;
   G is the goal for appointments;
   R is the number of available appointments; and
   $\epsilon$ is an adjustment for client perception of access (−0.1,0,0.1).

8. A process, as defined in claim 7 wherein said displaying step is performed on said graph by charting the cost performance characteristics such that are given by:

$$Cost = \sum_{i=1}^{2} (\beta_i I_i - \mu_i)$$

where:
i is an inhouse client indicator;
$\beta$ is an adjustment factor for case weight, severity, and a ratio of direct cost to total cost;
I direct cost per catchment area employee; and
$\mu$ is a benchmark cost against which facility costs are compared.

9. A process, as defined in claim 2 wherein said displaying step is performed on said graph by charting the cost performance characteristics such that are given by:

$$Cost = \sum_{i=1}^{2} (\beta_i I_i - \mu_i)$$

where:
i is an inhouse client indicator;
$\beta$ is an adjustment factor for case weight, severity, and a ratio of direct cost to total cost;
I direct cost per catchment area employee; and
$\mu$ is a benchmark cost against which facility costs are compared.

10. A process, as defined in claim 1, wherein said displaying step is performed on said graph by charting the quality performance characteristics such that:

$$Quality = \sum_{i=1}^{10} \left( \frac{\beta_i I_i - \mu_i}{\sigma_i} \right) + \epsilon$$

where:
i is a quality indicator;
$\beta$ is an adjustment factor based on an average severity indexing for a particular treatment facility;
I is a quality indicator value at a particular treatment facility;
$\mu$ is a mean value of the QIP indicator for all treatment facilities;
$\sigma$ is a standard deviation for a QIP indicator based on all treatment facilities; and
$\epsilon$ is a patient perception adjustment factor $(-0.1, 0, 0.1)$.

11. A process, as defined in claim 10, wherein said displaying step is performed on said graph by charting the access performance characteristics such that:

$$Access = \sum_{i=1}^{2} \left( \frac{C_i + D_i - G_i R_i}{C_i} \right) + \epsilon$$

where
i indicates inhouse client;
C is a preselected average daily client load;
D is a particular hospital average daily client;
G is the goal for appointments;
R is the number of available appointments; and
$\epsilon$ is an adjustment for client perception of access $(-0.1, 0, 0.1)$.

12. A process, as defined in claim 11 wherein said displaying step is performed on said graph by charting the cost performance characteristics such that are given by:

$$Cost = \sum_{i=1}^{2} (\beta_i I_i - \mu_i)$$

where:
i is an inhouse client indicator;
$\beta$ is an adjustment factor for case weight, severity, and a ratio of direct cost to total cost;
I direct cost per catchment area employee; and
$\mu$ is a benchmark cost against which facility costs are compared.

13. A process, as defined in claim 10 wherein said displaying step is performed on said graph by charting the cost performance characteristics such that are given by:

$$Cost = \sum_{i=1}^{2} (\beta_i I_i - \mu_i)$$

where:
i is an inhouse client indicator;
$\beta$ is an adjustment factor for case weight, severity, and a ratio of direct cost to total cost;
I direct cost per catchment area employee; and
$\mu$ is a benchmark cost against which facility costs are compared.

14. A process, as defined in claim 1, wherein said displaying step is performed on said graph by charting the access performance characteristics such that:

$$Access = \sum_{i=1}^{2} \left( \frac{C_i + D_i - G_i R_i}{C_i} \right) + \epsilon$$

where
i indicates inhouse client;
C is one facility average daily client load;
D is another facility daily client load;
G is the goal for appointments;
R is the number of available appointments; and
$\epsilon$ is an adjustment for client perception of access $(-0.1, 0, 0.1)$.

15. A process, as defined in claim 14 wherein said displaying step is performed on said graph by charting the cost performance characteristics such that are given by:

$$Cost = \sum_{i=1}^{2} (\beta_i I_i - \mu_i)$$

where:
i is an inhouse client indicator;
$\beta$ is an adjustment factor for case weight, severity, and a ratio of direct cost to total cost;
I direct cost per catchment area employee; and
$\mu$ is a benchmark cost against which facility costs are compared.

16. A process, as defined in claim 1 wherein said displaying step is performed on said graph by charting the cost performance characteristics such that are given by:

$$\text{Cost} = \sum_{i=1}^{2} (\beta_i I_i - \mu_i)$$

where:

i is an inhouse client indicator;

$\beta$ is an adjustment factor for case weight, severity, and a ratio of direct cost to total cost;

I direct cost per catchment area employee; and $\mu$ is a benchmark cost against which facility costs are compared.

17. A system for evaluating effectiveness of service among a set of treatment facilities, said system comprising:

a means for gathering data quantifying quality, cost, and access performances characteristics of each of the treatment facilities;

a means for displaying the quality, cost and access performance characteristics simultaneously on a graph to indicate thereby strong and weak quality, cost and access performance characteristics; and a means for identifying the strong and weak quality, cost and access performance characteristics of each treatment facility.

18. A system, as defined in claim 17, wherein said displaying means comprises a computer monitor which is connected to a computer which is programmed to depict the quality, cost and access performance characteristics in a chart that simulates a three-dimensional cube which has a separate axis for the quality, cost, and access performance characteristics.

* * * * *